US006241985B1

(12) United States Patent
Madiyalakan et al.

(10) Patent No.: US 6,241,985 B1
(45) Date of Patent: Jun. 5, 2001

(54) METHOD AND COMPOSITION FOR RECONFORMING MULTI-EPITOPIC ANTIGENS TO INITIATE AN IMMUNE RESPONSE

(75) Inventors: Ragupathy Madiyalakan; Antoine A. Noujaim, both of Edmonton (CA); Richard P. Baum, Frankfurt (DE); Birgit Schultes, Edmonton (CA)

(73) Assignee: Altarex Corp., Waltham, MA (US)

( * ) Notice: Subject to any disclaimer, the term of this patent is extended or adjusted under 35 U.S.C. 154(b) by 0 days.

(21) Appl. No.: 08/913,290

(22) PCT Filed: May 15, 1996

(86) PCT No.: PCT/IB96/00461

§ 371 Date: Mar. 20, 1998

§ 102(e) Date: Mar. 20, 1998

(87) PCT Pub. No.: WO97/42973

PCT Pub. Date: Nov. 20, 1997

(51) Int. Cl.[7] .................................................. A61K 39/395
(52) U.S. Cl. .................................... 424/130.1; 424/131.1; 424/138.1; 424/141.1; 424/152.1; 424/155.1; 424/156.1; 424/172.1; 424/174.1
(58) Field of Search .............................. 424/130.1, 131.1, 424/138.1, 141.1, 152.1, 155.1, 156.1, 172.1, 174.1

(56) References Cited

U.S. PATENT DOCUMENTS

| 4,940,670 | 7/1990 | Rhodes . |
| 4,950,480 | 8/1990 | Barber et al. . |
| 4,997,762 | 3/1991 | Hanna, Jr. et al. . |
| 5,009,888 | 4/1991 | Dunn . |
| 5,013,547 | 5/1991 | Sweet et al. . |
| 5,053,224 | 10/1991 | Koprowski et al. . |
| 5,183,657 | 2/1993 | Buurman . |
| 5,194,254 | 3/1993 | Barber et al. . |
| 5,308,614 | 5/1994 | Hakomori . |
| 5,389,530 | 2/1995 | Hakomori . |
| 5,478,556 | 12/1995 | Elliott et al. . |
| 5,500,215 | 3/1996 | Hakomori . |
| 5,518,723 | 5/1996 | Devico et al. . |

FOREIGN PATENT DOCUMENTS

| 0288082 | 4/1988 | (EP) . |
| WO89/01629 | 2/1989 | (WO) . |
| PCT/US90/03142 | 6/1990 | (WO) . |
| PCT/US92/11334 | 7/1993 | (WO) . |
| PCT/EP94/01719 | 8/1994 | (WO) . |

OTHER PUBLICATIONS

R. Madiyalakan, et al., Hybridoma, 14: 199–203 (1995).
C. A. Ghiron et al., Photochemistry and Photobiology, 7: 87–92 (1968).
Kristina N. Prodouz et al., Blood 70: 589–592 (1987).
S. A. Jose et al., Molecular Immunology, 24: 1145–1150 (1987).
A. Kleckowski et al., Photochem. Photobiol., 1: 299–304 (1962).
Roderick Murray et al., J.A.M.A., 8–14 (1955).
N.R. Kallenbach et al., Curr Stud Hematol Blood Transfus., 70–82 (1989).
Thomas R. Sykes et al., The Journal of Nuclear Medicine 36: 1913–1922 (1995).
R.P. Baum et al., Hybridoma, 12: 583–589 (1993).
R.P. Baum, M.D. et al., Cancer, 73:1121–1125 (1994).
A.A. Noujaim et al., Current Tumor Diagnosis, 823–829 (1994).
Malaya Bhattacharya Chatterjee et al., Cancer Immunol Immunother 38: 75–82(1994).
A. W. Thomson et al., Clin Exp Immunol 98: 351–357 (1994).
Sean Kehoe, International Journal of Oncology 6: 451–458 (1995).
Antonio Lanzavecchia, Science, 260: 937–944 (1993).
Uwe A. Wagner et al., Biotechnology Therapeutics, 3: 81–89 (1992).
Nemazee et al., PNAS, 79: 3828–3832 (1982).
Freda K. Stevenson et al., Immunol., 2: 16–19 (1994).
Leoni et al., Int. J. Cancer 40: 592–597 (1987).
Imai et al (Acta Pathol., Jpn., 29:43–49), 1989.*
Gura (Science, 278:1041–1042), 1997.*
Herbert et al (Dictionary of Immunology, Academic Press, London, pp 58, 59, 72, 73 and 154), 1995.*

* cited by examiner

Primary Examiner—Susan Ungar
(74) Attorney, Agent, or Firm—Hale and Door LLP (57) ABSTRACT

The invention concerns methods and compositions for intiating and/or enhancing an immune response by contacting a binding reagent with a soluble antigen, wherein the binding reagent-antigen pair generates an immune response to the antigen.

14 Claims, 3 Drawing Sheets

METHOD AND COMPOSITION FOR RECONFORMING MULTI-EPITOPIC ANTIGENS TO INITIATE AN IMMUNE RESPONSE

BACKGROUND OF THE INVENTION

1. Field of the Invention

The invention concerns methods and compositions for initiating and/or enhancing an immune response in vivo.

2. Summary of the Related Art

All vertebrates have an immune system. The ability of vertebrates to protect themselves against infectious microbes, toxins, viruses, or other foreign macromolecules is referred to as immunity. Immunity is highly specific; such specificity is a fundamental characteristic of immune responses. Many of the responses of the immune system initiate the destruction and elimination of invading organisms and any toxic molecules produced by them. Because the nature of these immune reactions is inherently destructive, it is essential that the response is precisely limited to the foreign molecules and not to those of the host itself. This ability to distinguish between foreign molecules and self molecules is another fundamental feature of the immune system.

The art distinguishes between natural and acquired or specific immunity. Natural immunity is comprised of defense mechanisms which are active before exposure to microbes or foreign macromolecules, are not enhanced by such exposure, and do not distinguish among most substances foreign to the body. Effectors of natural immunity are physical barriers such as skin or mucous membranes, phagocytic cells such as macrophages or neutrophils, a class of lymphocytes termed natural killer cells, and the complement system. Complement is a serum protein complex that is destructive to certain bacterial and other cells sensitized by specific, complement-fixing antibodies; its activity is effected by a series of interactions resulting in proteolytic cleavages and which can follow one or the other of at least two pathways.

In vertebrates, the mechanisms of natural and specific immunity cooperate within a system of host defenses, the immune system, to eliminate foreign invaders. In addition to microbes, cancer cells, parasites and virus-infected cells, the immune system also recognizes and eliminates cells or tissues transplanted into a subject from a genetically different individual of the same species (allografts) or from a different species (xenografts).

Acquired or specific immunity comprises defense mechanisms which are induced or stimulated by exposure to foreign substances. The events by which the mechanisms of specific immunity become engaged in the defense against foreign substances are termed immune responses. Vertebrates have two broad classes of immune responses: antibody responses, or humoral immunity, and cell-mediated immune responses, or cellular immunity. Humoral immunity is provided by B lymphocytes, which, after proliferation and differentiation, produce antibodies (proteins also known as immunoglobulins) that circulate in the blood and lymphatic fluid. These antibodies specifically bind to the antigen that induced them. Binding by antibody inactivates the foreign substance, e.g., a virus, by blocking the substance's ability to bind to receptors on a target cell. The humoral response primarily defends against the extracellular phases of bacterial and viral infections. In humoral immunity, serum alone can transfer the response, and the effectors of the response are soluble protein molecules called antibodies.

The second class of immune responses, cellular immunity, involve the production of specialized cells, e.g., T lymphocytes, that react with foreign antigens on the surface of other host cells. The cellular immune response is particularly effective against fungi, parasites, intracellular viral infections, cancer cells and other foreign matter. In fact, the majority of T lymphocytes play a regulatory role in immunity, acting either to enhance or suppress the responses of other white blood cells. These cells, called helper T cells and suppressor T cells, respectively, are collectively referred to as regulatory cells. Other T lymphocytes, called cytotoxic T cells, kill virus-infected cells. Both cytotoxic T cells and B lymphocytes are involved directly in defense against infection and are collectively referred to as effector cells.

The time course of an immune response is subdivided into the cognitive or recognition phase, during which specific lymphocytes recognize the foreign antigen; the activation phase, during which specific lymphocytes respond to the foreign antigen; and the effector phase, during which antigen-activated lymphocytes mediate the processes required to eliminate the antigen. Lymphocytes are immune cells that are specialized in mediating and directing specific immune responses. T cells and B cells become morphologically distinguishable only after they have been stimulated by an antigen.

The immune system has evolved so that it is able to recognize surface features of macromolecules that are not normal constituents of the host. As noted above, a foreign molecule which is recognized by the immune system (i.e., bound by antibodies), regardless of whether it can itself elicit a response is called an "antigen", and the portion of the antigen to which an antibody binds is called the "antigenic determinant", or "epitope". Some antigens, e.g., tumor-associated antigens such as ovarian cancer or breast cancer antigens, have multiple antibody binding sites. These antigens are termed "multi-epitopic" antigens. When the antigen is a polypeptide, it is customary to classify epitopes as being linear (i.e., composed of a contiguous sequence of amino acids repeated along the polypeptide chain) or nonlinear (i.e., composed of amino acids brought into proximity as a result of the folding of the polypeptide chain). Nonlinear epitopes are also called "conformational" because they arise through the folding of the polypeptide chain into a particular conformation, i.e., a distinctive 3-D shape. Because of the highly specific nature of the antibody-antigen bond, a primary means of distinguishing between antigens, or between different epitopes on the same antigen, is by antibody binding properties.

To cope with the immense variety of epitopes encountered, the immune system of a mammalian individual contains an extremely large repertoire of lymphocytes, approximately $2\times10^{12}$. Each lymphocyte clone of the repertoire contains surface receptors specific for one epitope. It is estimated that the mammalian immune system can distinguish at least $10^8$ distinct antigenic determinants. Even a single antigenic determinant will, in general, activate many clones, each of which produces an antigen-binding site with its own characteristic affinity for the determinant. Antigens that stimulate the production of hundreds of species of antibodies, each made by a different B cell clone, are said to produce a polyclonal response. When only a few clones respond, the response is said to be oligoclonal; when the total response is made by a single B or T cell clone, the response is said to be monoclonal. The response to most antigens are polyclonal.

An initial or primary immune response to a foreign antigen enhances the ability of the immune system to respond again to that antigen. This feature of specific immunity is called immunologic memory, or a secondary immune response. Secondary immune responses are often more effective than primary responses.

The conventional definition of an antigen is a substance that can elicit in a vertebrate host the formation of a specific antibody or the generation of a specific population of lymphocytes reactive with the substance. As frequently occurs in science, however, it is now known that this definition, although accurate, is not complete. For example, it is now known that some disease conditions suppress or inactivate the host immune response. Under these conditions, a tumor antigen does not elicit an antibody or generate specific lymphocytes. Thus, not all antigens are capable of eliciting a human immune response.

The failure in the definition centers on a two-part aspect of the immune response: the first step in the immune response is the recognition of the presence of a foreign entity; the second step is a complex array or cascade of reactions, i.e., the response. In the tumor antigen example given above, the immune system can recognize the presence of a foreign antigen, but it cannot respond. In another example, a failure in the immune system's ability to distinguish between self and non-self appears to be at the origin of many autoimmune diseases. Again, this is a failure in recognition, not response.

As used herein, therefore, if an antigen can be recognized by the immune system, it is said to be antigenic. If the immune system can also mount an active response against the antigen, it is said to be immunogenic. Antigens which are immunogenic are usually macromolecules (such as proteins, nucleic acids, carbohydrates and lipids) of at least 5000 Daltons molecular weight. Smaller nonimmunogenic molecules, e.g., haptens and small antigenic molecules, can stimulate an immune response if associated with a carrier molecule of sufficient size.

Antibodies, the effectors of humoral immunity, are secreted by plasma cells, and are among the most abundant components of the blood. Plasma cells are mature end stage cells that appear to have a relatively short life span. They are produced when an antigen enters the human immune system and, in a complex series of cell interactions, activates B lymphocytes. B lymphocytes then proliferate and differentiate to form plasma cells. Each B lymphocyte is programmed by its DNA to make an antibody molecule of a single specificity. B lymphocytes make two special forms of this molecule, one that remains anchored to the outer surface of the cell membrane as a membrane receptor, typically for binding antigen to the B cell, and one that is secreted.

Antibodies, also known as immunoglobulins, are proteins. They have two principal functions. The first is to recognize (bind) foreign antigens. The second is to mobilize other elements of the immune system to destroy the foreign entity.

The antigen recognition structures of an antibody are variable domains, and are responsible for antigen binding. The immune system mobilization structures, the second function of the antibody, are constant domains; these regions are charged with the various effector functions: stimulation of B cells to undergo proliferation and differentiation, activation of the complement cell lysis system, opsonization, attraction of macrophages to ingest the invader, etc. Antibodies of different isotypes have different constant domains and therefore have different effector functions. The best studied isotypes are IgG and IgM.

The antibody itself is an oligomeric molecule, classified, according to its structure, into a class (e.g., IgG) and subclass (e.g., IgG1). IgG molecules are the most important component of the humoral immune response and are composed of two heavy (long) and two light (short) chains, joined by disulfide bonds into a "Y" configuration. The molecule has two variable regions (at the arms of the "Y"). The regions are so named because antibodies of a particular subclass, produced by a particular individual in response to different antigens, will differ in the variable region but not in the constant regions. The variable regions themselves are composed of both a relatively invariant framework, and of hypervariable loops, which confer on the antibody its specificity for a particular epitope. An antibody binds to an epitope of an antigen as a result of molecular complementarity. The portions of the antibody which participate directly in the interaction is called "antigen binding site", or "paratope". The antigens bound by a particular antibody are called its "cognate antigens".

An antibody of one animal will be seen as a foreign antigen by the immune system of another animal, and will therefore elicit an immune response. Some of the resulting antibodies will be specific for the unique epitopes (idiotype) of the variable region of the immunizing antibody, and are therefore termed anti-idiotypic antibodies. These often have immunological characteristics similar to those of an antigen cognate to the immunizing antibody. Anti-isotypic antibodies, on the other hand, bind epitopes in the constant region of the immunizing antigen.

As noted above, the cells that regulate cell-mediated immunity are a class of lymphocytes called T lymphocytes. They arise ultimately from the same stem cell as B lymphocytes, however, they follow a very different pathway of development in which the thymus plays an important role. T lymphocytes also express antigen specific surface receptors although the way in which they recognize antigens is rather different than for B cells. T cells exist in 2 functional categories: those with a specific effector function (cytotoxic T lymphocytes or "CTL") and those with regulatory function. Regulatory T cells are required for the development of plasma cells from B cells. T helper cells (TH) produce an antigen specific up-regulation of the immune response. Immune responses can also undergo active antigen specific down regulation. A large body of evidence from studies with animals and tissue culture describes the presence of a suppressor T cell population (TS) that provides this inhibitory regulation.

The lymphocytes in an individual specifically respond to foreign antigens but are usually unresponsive to the potentially antigenic substances native to that individual. Immunologic unresponsiveness is referred to as tolerance. self-tolerance is acquired at an early developmental stage when potentially self-recognizing lymphocytes come into contact with self-antigens and are prevented from developing to a stage at which they would be able to respond positively to self antigens.

The immune system has two cytokine-mediated regulatory pathways that determine whether the response to antigenic challenge will be principally a cellular response (TH1 pathway) or principally a humoral response (TH2 pathway). The cellular pathway is characterized by the T helper cell production of interleukin-2 (IL-2) or interferon-γ. This pathway mediates the delayed type hypersensitivity (DTH) response, the generation of cytotoxic T cells, and macrophage activation. The TH2 response promotes the production by T cells of a variety of cytokines, such as interleukin-4 (IL-4) and interleukin-10 (IL-10). This response is identified by the production of specific antibodies in high titre.

The tendency for either the cell-mediated or humoral immune response to predominate is believed to be a consequence of cross-regulation. Thus TH1 cells would inhibit the elicitation of TH2 responses, e.g., by secretion of interferon-γ. Conversely, TH2-cells could inhibit the generation of TH1-responses by producing cytokines such as IL-4 and IL-10.

TH2 responses might actually exacerbate the development of certain diseases. It is well known in the art that injections of small amounts of immunizing antigens will preferentially elicit delayed-type hypersensitivity responses, indicative of cell-mediated immunity, whereas vaccination with larger amounts of antigen will result in a more pronounce humoral immune response as reflected by high antibody titre. However, it is difficult to avoid a high IgG response, and achieve a high and prolonged cellular response, by this method, and depending on the antigen, small doses may be insufficient to elicit a sufficiently strong CMI response to be useful.

Normally, an immune response progresses toward effector mechanisms characteristic of both B and T-lymphocytes. However, in the course of most immune responses, either B or T lymphocytes assume a dominant role, with less substantial participation of the respective other type of lymphocyte. Immune responses whose effector mechanisms are mediated preponderantly through B-cells and antibodies are humoral immune responses. Those responses wherein T-cells mediate the more important effector functions are cell-mediated or cellular immune responses.

As noted above, the cells that regulate humoral immunity are a class of lymphocytes called B-cells. Each clone of B-lymphocytes expresses membrane immunoglobulins (membrane Ig's, surface-bound antibody molecules) that function as antigen receptors having one unique epitope for one B-lymphocyte clone. These membrane Ig molecules are the sole source of B-cell specificity. Antigens that contain an epitope complementary to the membrane Ig will bind to the antigen receptor. Such antigens are also referred to as cognate antigens of the antibody. Binding to the antigen receptor (membrane Ig) will result in differentiation and clonal proliferation of the B-lymphocyte. Some of its progeny will differentiate into mature plasma cells which are specialized in the synthesis of antibodies corresponding in epitope specificity to the membrane Ig by which the B-lymphocyte had initially bound the antigen.

The binding of an antigen to an antibody is reversible. It is mediated by the sum of many relatively weak non-covalent forces, including hydrophobic and hydrogen bonds, vander Waals forces, and ionic interactions. These weak forces are effective only when the antigen molecule is close enough to allow some of its atoms to fit into complementary recesses on the surface of the antibody. The complementary regions of a four-chain antibody unit are its two identical antigen-binding sites; the corresponding region on the antigen is an antigenic determinant. Many antigenic macromolecules have many different antigenic determinants.

For many years, live, attenuated vaccines have been used to induce immunity against viral infections such as influenza and polio. These preparations contain live virions which cause mild, subclinical infections of the vaccinated individuals. In the course of such infections, viral vectors will enter certain host cells and code for the synthesis of virus-specific proteins. These endogenously produced antigenic proteins are processed into smaller peptides and presented in the context of MHC Class I and II antigens, thereby recruiting TH1 cells and eliciting cell-medicated immune responses.

Tumor cells express certain cell surface antigens ("tumor-associated antigens"). Tumor-associated antigens are antigens that are present in the serum and tissues of cancer patients. Many such antigens are also expressed in embryonic tissues, and, at low levels, in the tissue and serum of healthy individuals. Many of the tissue-associated antigens are glycoproteins, glycolipids, or mucopolysaccharides. Most tumor antigens are produced by differentiated cells. They are produced in much larger quantities by tumor cells than by differentiated normal cells. The human immune system recognizes the tumor antigens as native antigens and does not respond ("self-tolerance"). The mechanisms leading to self-tolerance are only partly understood, but it is now clear that it is largely established during development of the immune system. If immature B cells or T cells are stimulated through their antigen specific receptors at a critical stage (e.g., just after expressing their receptors on the cell surface but before becoming mature), they are induced to die rather than to become activated. This stage occurs in the bone marrow for B cells and in the thymus for T cells. Tolerance thus will be induced to self-antigens expressed in these environments, but not to those that are not expressed. It has been shown that normal individuals have mature B cells capable of recognizing some self-antigens but that these B cells are not activated. The appropriate T helper cells (TH) appear to be missing.

For tumors that have antigens, there are at least four theories why the immune response may fail to destroy a tumor: 1) there are no B cells or cytotoxic T lymphocytes (CTL) capable of recognizing the tumor; 2) there are no TH cells capable of recognizing the tumor; 3) TS cells become activated before TH cells, thus preventing B-cell and CTL activation; and 4) the genes regulating tumor proliferation may be present from birth, so the host does not treat the gene products as "foreign."

Where tumor antigens appear with sufficient selectivity on a tumor (i.e., the tumor antigens are absent from or present only in small amounts on their normal cellular counterparts), the tumor antigen may serve as a possible target for an immunotherapeutic agent.

Many of these selective tumor antigens are carbohydrate or glycoprotein (mucin) in nature. For example, most adenocarcinoma cells abundantly express and secrete mucins. This is due in part to defects in glycosylation in cancer cells. Carcinoma cell surface mucins can physically block immune effector mechanisms from reaching the tumor cell surface and, therefore, the tumor antigen. That is, the host fails to recognize the tumor antigen.

In many diseases, the causative pathogens or toxins (e.g., influenza, polio, and rabies viruses; pneumococcus bacteria; diphtheria and tetanus toxins) can be effectively targeted and neutralized in the extracellular fluid by the mechanisms of humoral immunity through antibodies that bind to the pathogens or toxins and thereby lead to their inactivation of destruction. In these cases, vaccination with preparations that elicit a humoral immune response, presumably mediated by TH2 cells, is generally sufficient for protection. On the other hand, for many intracellular infections,. for recovery from viral infections, and for targeted killing of cancer cells, it is cell-mediated immunity that protects the organism against the invaders.

Three classes of immunotherapy are currently under investigation: 1) passive immunotherapy; 2) active immunotherapy with antigens; and 3) active immunotherapy with antibodies. Unfortunately, each has met with limited success. Immunotherapy, however, is preferred over antiproliferative chemotherapeutic agents, such as pyrimidine or purine analogs, in certain stages of cancer. The analogs compete with pyrimidine and purine as building blocks used during a cell's growth cycle. The analogs are ineffective where growth is non-cycling or dormant. The majority of micrometastatic cells appear to be non-cycling or dormant. The cytotoxic effect of immunotherapy operates independently of cell cycle.

"Passive immunotherapy" involves the administration of antibodies to a patient. Antibody therapy is conventionally characterized as passive since the patient is not the source of the antibodies. However, the term passive is misleading because the patient can produce anti-idiotypic secondary antibodies which in turn can provoke an immune response which is cross-reactive with the original antigen. "Active immunotherapy" is the administration of an antigen, in the form of a vaccine, to a patient, so as to elicit a protective immune response. Genetically modified tumor cell vaccines transfected with genes expressing cytokines and co-stimulatory molecules have also been used to alleviate the inadequacy of the tumor specific immune response.

A tumor antigen can serve as a reactive site to which antibodies can become bound. Numerous antibodies have been raised against tumor antigens.

Conventional effector methods include complement dependent cytolysis ("CDC"), antibody dependent cellular cytotoxicity ("ADCC") and phagocytosis (clearance by reticuloendothelial system after the target cell is coated with immunoglobulin).

A relatively large quantity of antibody is required to initiate CDC, ADCC and opsonization. Furthermore, sources of human antibodies are limited to people already suffering from the tumor of interest; it is unethical to introduce a disease into a person merely to initiate production of antibodies which may be harvested. As a result of these difficulties, antibodies of non-human origin, such as mouse antibodies, have been used.

The administration to humans of mouse antibodies, because they are recognized as "foreign," can provoke a human anti-mouse antibody response ("HAMA") directed against mouse-specific and mouse isotype-specific portions of the primary antibody molecule. This immune reaction occurs because of differences in the primary amino acid sequences in the constant regions of the immunoglobulins of mice and humans. Both IgG and IgM subclasses of HAMA have been detected. The IgG response appears later, is longer-lived than the typical IgM response, and is more resistant to removal by plasmapheresis.

Clinically, however, HAMA: 1) increases the risk of anaphylactic or serum sickness-like reactions to subsequent administration of mouse antibodies; 2) can interfere with the immunotherapeutic effect of subsequently injected mouse antibodies by complexing with those antibodies, increasing clearance from the body, reducing tumor localization, enhancing uptake into the liver and spleen, and/or hiding the tumor from therapeutic agents; and 3) can interfere with immunodiagnostic agents and thereby hinder monitoring of the progress of the disease and course of treatment.

Various clinical trials have used antibodies as therapeutic agents against solid tumors. No consistent pattern of response or improved survival has yet emerged. By contrast, antibody therapy has more often induced complete and long-lasting remissions in B-cell or T-cell lymphomas or leukemias. Explanations for solid tumor failures include antigenic heterogeneity and insufficient accessibility of epithelial cells to the injected antibodies as well as to secondary effector molecules like complement or effector cells.

As an example of passive immunity, mouse monoclonal antibody 17-1A (isotype IgG2a) was used to target minimal residual disease in patients with Duke's stage C colorectal cancer who had undergone curative surgery and were free of manifest residual tumor. Although the treatment improved survival and led to reduced recurrence rates, the results were less favorable than treatment with chemotherapy alone, or in combination with radiation.

It is important to note that the target antigen for 17-1A is not shed from the membrane and is not detectable in serum. See Riethmüller, et al., "Randomized trial of monoclonal antibody for adjuvant therapy of resected Dukes' C colorectal carcinoma", *Lancet*, 343:1177–83 (1994).

ASI is defined as immunization with a defined antigen, presented in an appropriate manner, to actively induce an immune response specifically to that antigen. In the context of cancer, ASI attempts to stimulate a human immune response, both humoral and cell-mediated, to attack the tumor antigen.

The humoral response and the conventional effector methods of CDC, ADCC and phagocytosis (clearance by reticuloendothelial system after the target cell is coated with immunoglobulin) were discussed above.

Over the past 5 years, considerable progress has been made in the characterization of the molecular complex recognized by the specific antigen receptor of T lymphocytes. Crystal structures of class I major histocompatibility complex ("MHC") molecules revealed not only a putative peptide binding groove but also the actual presence in this groove of a peptide. After phagocytosis, proteins synthesized within the cells apparently are degraded into peptides by cellular enzymes, transported into the endoplasmic reticulum, and there, combine with the heavy chain of a class I MHC molecule. Such peptide-MHC complexes are stabilized by the addition of $\beta$2-microglobulin and transported to the cell surface where they can be recognized by the receptor of CTL. In theory, an antigenic peptide can be derived from any intracellular protein specifically expressed by tumor cells. See, for example, Van Der Bruggen, Pierre, "The Long-Standing Quest for Tumor Rejection Antigens," *Clinical Immunology and Immunopathology*, 71; 3:248–252 (1994).

If a specific antibody from one animal is injected as an immunogen into a suitable second animal, the injected antibody will elicit an immune response (e.g., produced antibodies against the injected antibodies—"anti-antibodies"). Some of these anti-antibodies will be specific for the unique epitopes (idiotopes) of the variable domain of the injected antibodies. These epitopes are known collectively as the idiotype of the primary antibody; the secondary (anti-) antibodies which bind to these epitopes are known as anti-idiotypic antibodies. The sum of all idiotopes present on the variable portion of an antibody is referred to as its idiotype. Idiotypes are serologically defined, since injection of a primary antibody that binds an epitope of the antigen may induce the production of anti-idiotypic antibodies. When binding between the primary antibody and an anti-idiotypic antibody is inhibited by the antigen to which the primary antibody is directed, the idiotype is binding site or epitope related. Other secondary antibodies will be specific for the epitopes of the constant domains of the injected antibodies and hence are known as anti-isotypic antibodies. As used herein, anti-idiotype, anti-idiotypic antibody, epitope, or epitopic are used in their art-recognized sense.

The "network" theory states that antibodies produced initially during an immune response will carry unique new epitopes to which the organism is not tolerant, and therefore will elicit production of secondary antibodies (Ab2) directed against the idiotypes of the primary antibodies (Ab1). These secondary antibodies likewise will have an idiotype which will induce production of tertiary antibodies (Ab3) and so forth.

$$Ab_1 \rightarrow Ab_2 \rightarrow Ab_3$$

The network theory also suggests that some of these secondary antibodies (Ab2) will have a binding site that is the complement of the complement of the original antigen and thus will reproduce the "internal image" of the original antigen. In other words, an anti-idiotypic antibody may be a surrogate antigen.

A traditional approach to cancer immunotherapy has been to administer anti-tumor antibodies, i.e., antibodies which recognize an epitope on a tumor cell, to patients. However, the development of the "network" theory led investigators to suggest the direct administration of exogenously produced anti-idiotype antibodies, that is, antibodies raised against the idiotype of an anti-tumor antibody. Such an approach is disclosed in U.S. Pat. No. 5,053,224 (Koprowski, et al.) Koprowski assumes that the patient's body will produce anti-antibodies that will not only recognize these anti-idiotype antibodies, but also the original tumor epitope.

There are four major types of anti-idiotypic antibodies. The alpha-type binds an epitope remote from the paratope of the primary antibody. The beta-type is one whose paratope always mimics the epitope of the original antigen. The gamma-type binds near enough to the paratope of the primary antibody to interfere with antigen binding. The epsilon-type recognizes an idiotypic determinant that mimics a constant domain antigenic structure. Moreover, anti-isotypic antibodies may be heavy chain-specific or light chain-specific.

Two therapeutic applications arose from the network theory: 1) administer Ab1 which acts as an antigen inducing Ab2 production by the host; and 2) administer Ab2 which functionally imitates the tumor antigen.

Active immunization of ovarian cancer patients with repeated intravenous applications of the F(Ab')$_2$ fragments of the monoclonal antibody OC125 was reported to induce remarkable anti-idiotypic antibody (Ab2) responses in some of the patients. Preliminary results suggested that patients with high Ab2 serum concentrations had better survival rates compared to those where low or no Ab2 serum levels were detected. See Wagner, U. et al., "Clinical Course of Patients with Ovarian Carcinomas After Induction of Anti-idiotypic Antibodies Against a Tumor-Associated Antigen," *Tumor Diagnostic & Therapie*, 11:1–4, (1990).

A human anti-idiotypic monoclonal antibody (Ab2) has been shown to induce anti-tumor cellular responses in animals and appears to prolong survival in patients with metastatic colorectal cancer. See Durrant, L. G. et al., "Enhanced Cell-Mediated Tumor Killing in Patients Immunized with Human Monoclonal Anti-Idiotypic Antibody 105AD7," *Cancer Research*, 54:4837–4840 (1994). The use of anti-idiotypic antibodies (Ab2) for immunotherapy of cancer is also reviewed by Bhattacharya-Chatterje, et al; *Cancer Immunol. Immunother.* 38:75–82 (1994).

BRIEF SUMMARY OF THE INVENTION

Vaccines are preparations administered to animals or humans to effect the prophylaxis, cure or alleviation of disease states through induction of specific immunity. Prophylactic vaccines are given to healthy individuals with the intention of preparing or priming the immune system for more effective defense against infections in the future. In the event of an infection or infestation, the immune system of vaccinated individual can mount a secondary immune response and can more rapidly recognize and eliminate the respective pathogens. Therapeutic vaccines are given to diseased individuals with the intent of stimulating or modulating the immune system which of itself has either mounted an insufficiently effective immune response or has altogether failed to respond. In the design of prophylactic or therapeutic vaccines, it is important to choose preparations that will elicit the type of immune response most capable of either providing first-line protection, or effecting speedy recovery.

The first step in initiating an immune response is generating host recognition of the tumor antigen as a foreign antigen. For example, although CA125 expression is associated with ovarian cancer, the patient's immune system fails to recognize it as foreign. The present invention involves contacting a soluble antigen with a composition of the invention, and reacting a binding agent in the composition with the soluble antigen. In accordance with the invention, binding the antigen with the binding agent generates host recognition of the antigen. In turn, generating host recognition leads to initiating an immune response against the antigen.

The present invention involves the discovery that binding a binding agent to a pre-determined epitope of a multi-epitopic tumor-associated antigen alters the antigen in a manner so that the host immune system can recognize and initiate an immune response to the previously unrecognized antigen. In one embodiment of the invention, a binding agent binds to a soluble tumor associated antigen, allowing the host immune system to generate a response against the antigen. For example, illustrative of the present invention is B43.13, an antibody binding agent that binds specifically to ovarian cancer antigen CA 125 at the 43.13 epitope. Once B43.13 binds to the CA 125 antigen, either the conformation of the antigen is altered or the antigen is processed and/or delivered differently to that it is recognized by the host's immune system. Antibody B43-13 was deposited under the Budapest Treaty in the ATCC, 1801 University Blvd., Manassas, Va. 20110-2209 and given the Patent Deposit Designation PTA-1883 on May 18, 2000. Other examples include, but are not limited to a binding agent that binds specifically to CA19.9, a gastrointestinal antigen associated with gastrointestinal cancer; and to a binding agent that binds specifically to CA15.3, an antigen associated with breast cancer.

DETAILED DESCRIPTION OF THE PREFERRED EMBODIMENTS

In accordance with the present invention, a binding agent (s) and compositions comprising such binding agents are provided, wherein the binding agent binds selectively to a pre-determined soluble antigen, and wherein such binding event results in the presentation of a different epitope on the-antigen, said different epitope resulting in an immune response that inhibits or kills the cells that produced the antigen.

In a preferred embodiment of the invention, a composition comprising a pre-determined antibody that specifically binds to a pre-determined tumor associated antigen is used to bind a soluble antigen produced by the tumor. Once the soluble antigen is bound, the immune system recognizes the antigen as "foreign," and mounts an immune response against the antigen or against the binding agent bound to the antigen. Antigens that can be made immunogenic are potentially useful to induce or activate an immune response, leading to therapeutic and possibly prophylactic benefits.

For diseases that can be characterized in part by having a tumor-associated antigen that is multi-epitopic, the present invention involves contacting a soluble antigen with a binding reagent that specifically binds to a single epitope on the multi-epitopic tumor-associated antigen.

The binding agent may be directed against any antigen of clinical significance, but preferably is directed against a tumor-associated antigen (TAA). In the case of TAA, the cancer may include, but is not limited to lung, colon, rectum, breast, ovary, prostate gland, head, neck, bone, immune system, or any other anatomical location. The subject may be a human or animal subject. Illustrative tumors and tumor markers are listed in U.S. Pat. No. 5,075,218.

The methods of the present invention involve any cancer that produces a soluble multi-epitopic TAA. As used herein soluble is used to describe any antigen that is detectable in a body fluid, i.e., blood, serum, ascites, saliva, or the like. In accordance with the present invention, the preferred tumors are those that: shed soluble tumor antigens, e.g., tumor antigens shed into the bloodstream, as opposed to a surface antigen or an intracellular antigen; exhibit a multi-epitopic tumor associated antigen, preferably of carbohydrate or glycoprotein (e.g., mucin) nature; and can be found at a concentration in the patient's body fluid more than is normally present in healthy controls and such a high level signifies a poor prognosis for the patient, yet has not initiated an immune response. As is well known by one skilled in the art, one method of determining whether the concentration of the TAA is greater than is predictive of recurrence of the disease is by comparing the patient's concentration to that of a healthy control. If the concentration of the TAA is higher than the healthy control, then the patient's concentration is predictive of poor prognosis of the disease.

A binding agent (BA), as used herein, refers to one member of an immunologic pair, e.g., a binding moiety that is capable of binding to a single epitope expressed on the tumor antigen. Exemplary binding agents include, but are not limited to: monoclonal antibodies ("MAb"); chimeric monoclonal antibodies ("C-MAb"); genetically engineered monoclonal antibodies ("G-MAb"); fragments of monoclonal antibodies (including but not limited to "F(Ab)$_2$", "F(Ab)" and "Dab"); single chains representing the reactive portion of monoclonal antibodies ("SC-MAb"); tumor-binding peptides; any of the above joined to a molecule that mediates an effector function; and mimics of any of the above. The antibody may be a polyclonal antibody or a monoclonal antibody. When the subject is a human subject, the antibody may be obtained by immunizing any animal capable of mounting a usable immune response to the antigen, such as a mouse, rat, goat sheep, rabbit or other suitable experimental animal. In the case of a monoclonal antibody, antibody producing cells of the immunized animal may be fused with "immortal" or "immortalized" human or animal cells to obtain a hybridoma which produces the antibody. If desired, the genes encoding one or more of the immunoglobulin chains may be cloned so that the antibody may be produced in different host cells, and if desired, the genes may be mutated so as to alter the sequence and hence the immunological characteristics of the antibody produced. Fragments, or fragments of binding agents, may be obtained by conventional techniques, such as by proteolytic digestion of the binding agent using pepsin, papain, or the like; or by recombinant DNA techniques in which DNA encoding the desired fragment is cloned and expressed in a variety of hosts. Irradiating any of the foregoing entities, e.g., by ultraviolet light will enhance the immune response to a multi-epitopic antigen under similar conditions. In a preferred embodiment of the invention, effector functions that mediate CDC or ADCC are not required.

In an embodiment of the invention, a suitable composition for an ovarian tumor associated antigen contains a binding agent that binds the CA 125 antigen. In another embodiment of the invention, a suitable composition for gastrointestinal cancer contains a binding agent that binds the CA 19.9 antigen. In yet another embodiment of the invention, a suitable composition for breast cancer contains a binding agent that binds the CA 15.3 antigen. Various binding agents, antibodies, antigens, and methods for preparing, isolating, and using the antibodies are described in U.S. Pat. No. 4,471,057 (Koprowski) and U.S. Pat. No. 5,075,218 (Jette, et al.), both incorporated herein by reference. Furthermore, many of these antibodies are commercially available from Centocor, Abbott Laboratories, Commissariat a L'Energie Atomique, Hoffman-LaRoche, Inc., Sorin Biomedica, and FujiRebio.

Any composition that includes a binding agent according to the invention may be used to initiate an in vivo immune response. The composition may include one or more adjuvants, one or more carriers, one or more excipients, one or more stabilizers, one or more imaging reagents, and/or physiologically acceptable saline. Generally, adjuvants are substances mixed with an immunogen in order to elicit a more marked immune response. Control vaccinations without the adjuvant resulted in humoral immune responses. The composition may also include pharmaceutically acceptable carriers. Pharmaceutically accepted carriers include but are not limited to saline, sterile water, phosphate buffered saline, and the like. Other buffering agents, dispersing agents, and inert non-toxic substances suitable for delivery to a patient may be included in the compositions of the present invention. The compositions may be solutions suitable for administration, and are typically sterile and free of undesirable particulate matter. The compositions may be sterilized by conventional sterilization techniques.

In accordance with a method of the invention, the binding agent must contact and bind the tumor associated antigen, may be administered to the patient by any immunologically suitable route. For example, the binding agent may be introduced into the patient by an intravenous, subcutaneous, intraperitoneal, intradermal, intramuscular, or intralymphatic routes, in solution, tablet, or aerosol form. Liposomes, biodegradable microspheres, micelles, or the like may also be used as a carrier, vehicle, or delivery system. Furthermore, using ex vivo procedures well known in the art, blood or serum from the patient may be removed from the patient; optionally, it may be desirable to purify the antigen in the patient's blood; the blood or serum may then be mixed with a composition that includes a binding agent according to the invention; and the treated blood or serum is returned to the patient. The clinician may compare the anti-idiotypic and anti-isotypic responses associated with these different routes in determining the most effective route of administration. The invention should not be limited to any particular method of introducing the binding agent into the patient.

In accordance with the present invention, the BA-antigen interaction effectively presents the remaining epitopes to the patient's immune system to generate: 1) a humoral response resulting in human anti-tumor antibodies that may or may not be inhibitable by the injected antibody but are definitely inhibitable by an antibody which binds to an epitope different from the epitope reactive with the injected BA; and 2) a cell-mediated response resulting in the production of antigen-specific cytotoxic T-cells.

The binding agents of the present invention bind the multi-epitopic tumor antigen of interest, and the resulting immunogenic pair may be used toprime or initiate an immune response to another epitope on the antigen. As noted in more detail elsewhere in this disclosure, it is believed that the binding event between the binding agent and the multi-epitopic antigen changes the conformation of the antigen sufficiently to provide access to another previously unrecognizable epitope on the antigen. The previously unrecognizable epitope, once recognized by agents of the immune system, initiates the immune system cascade that results in an immune response to the whole antigen.

In accordance with an embodiment of the invention, a cancer patient with body fluid having endogenous, soluble multi-epitopic antigen is treated by injecting an exogenous binding agent directed to a single epitope of the endogenous soluble antigen. After binding, the antigen reconforms or is processed and/or delivered differently allowing a different epitope on the antigen to be presented to the patient's immune system. Upon presentation, the patient's immune system initiates and develops a humoral, cellular, or combined humoral/cellular response, leading to tumor killing and/or stasis. Evidence of the success of the present invention is shown in the Examples as improved survival times.

Without intending to be bound thereby, it is believed that a mechanism of action for the methods of the present invention involve a conformational alteration on the part of the soluble antigen bound by a binding agent according to the present invention. It is further believed that binding the antigen with a binding agent directed to a first epitope on the antigen changes the conformation of the antigen sufficiently to present or activate a second epitope. It is against this second epitope that the patient's immune system can respond. Alternatively, the binding agent—antigen interaction may lead to differential metabolic processing or delivery to the immune system in such a way to activate a second epitope.

DOSAGE

In accordance with the methods of the present invention, a composition comprising a binding agent may be administered in an amount sufficient to recognize and bind the pre-determined tumor associated antigen. In a preferred embodiment of the invention, the dosage is sufficient to generate or elicit an immune response against the TAA. An immunologically or therapeutically effective or acceptable amount of binding agent is an amount sufficient to bind a pre-determined antigen in vivo or ex vivo, and is capable of eliciting an immune response to the antigen. The response inhibits or kills tumor cells that carry and present a newly accessible epitope, thereby ameliorating or eliminating the disease or condition that produces the antigen. The immune response may take the form of a humoral response, a cell-mediated response, or both. In a preferred embodiment of the invention, the dosage of the monoclonal antibody is less than the dosage required to elicit ADCC or CDC.

The concentration or dosage of the binding agent or active agent in the composition can vary widely, e.g., from less than about 0.01% to about 15 to 20% by weight. As noted above, the composition is administered in an amount sufficient to stimulate an immune response against the antigen. Amounts effective for this use will depend in part on the severity of the disease and the status of the patient's immune system. Generally, the composition will include about 0.1 µg to about 2 mg or more of binding agent per kilogram of body weight, more commonly dosages of about 1 µg to about 200 µg per kilogram of body weight. The concentration will usually be at least 0.5%; any amount may be selected primarily based on fluid volume, viscosity, antigenicity, etc., in accordance with the particular mode of administration.

Administration may be more than once, preferably three times over a prolonged period. As the compositions of this invention may be used for patient's in a serious disease state, i.e., life-threatening or potentially life-threatening, excesses of the binding agent may be administered if desirable. Actual methods and protocols for administering pharmaceutical compositions, including dilution techniques for injections of the present compositions, are well known or will be apparent to one skilled in the art. Some of these methods and protocols are described in *Remington's Pharmaceutical Science*, Mack Publishing Co. (1982).

A binding agent may be administered in combination with other binding agents, or may be administered in combination with other treatment protocols or agents, e.g., chemotherapeutic agents.

The effectiveness of the binding agents of the present invention may be monitored in vitro or in vivo. Humoral responses may be monitored in vitro by conventional immunoassays, where the anti-tumor activity of the response may be determined by complement-mediated cellular cytotoxicity and/or antibody-dependent cellular cytotoxicity (ADCC) assays. The assay methodologies are well know, and are described in *Handbook of Experimental Immunology*, Vol. 2, Blackwell Scientific Publications, Oxford (1986). Other assays may be directed to determining the level of the antigen in the patient or tissue. Cell-mediated immunity may be monitored in vivo by the development of delayed-type hypersensitivity reactions, or other in vivo or in vitro means known to those skilled in the art, including but not limited to the skin test reaction protocol, lymphocyte stimulation assays, measuring the toxicity of a subject's lymphocytes to tumor cells by using a standard radioactive release assay, by a limiting dilution assay, or by measuring plasma levels of IL-2 using standard ELISA assays.

EXAMPLES

Example 1

Experimental Verification of the Generation of Antibody Response Against Multiple Epitopes Present in an Antigen by Injecting an Antibody Against a Single Epitope Cancer antigen CA125, which is expressed on more than 80% of epithelial ovarian cancers, is used as an example to demonstrate the present invention.

CA125 has multiple epitopes recognized by different antibodies such as OC125, M11, B43.13, B27.1, among others. In the present invention, MAb-B43.13 was used to generate a CA125 specific immune response which included recognition of the B27.1 epitope.

Method: 86 ovarian cancer patients with active disease were tested for the presence of antibodies against CA125. None of the patients had antibodies against CA125 before injection of MAb-B43.13. The patients were injected with 2 mg of MAb-B43.13 at varying time intervals (e.g., see Table 1 for some of the patients). Sera from these patients were analyzed for the presence of human anti-CA125 antibodies by their ability to bind to the CA125 [R. Madiyalakan et al, Hybridoma, 14:199–203 1995)]. Such anti-CA125 antibodies were further classified to be against the B43.13 epitope or B27.1 epitope by their ability to inhibit the corresponding antibodies. The rationale for the classification comes from the fact that anti-CA125 antibodies in these patients would have been generated by either of the following two pathways:

1) If the anti-CA125 antibodies were generated in the manner suggested by the network theory noted above, the pathway would follow Ab1→Ab2→Ab3. Following this scheme, MAb-B43.13 (Ab1) would generate an anti-idiotype against MAb-B43.13 (Ab2), which would in turn generate an anti-anti-idiotype against MAb-B43.13 (Ab3; or anti-CA125 antibody). Furthermore, the Ab3 antibodies generated under this pathway would bind and be inhibited only by MAb-B43.13, because the B43.13 epitope is the only epitope present.

2) If the anti-CA125 antibodies were generated in a manner suggested by the present invention, the pathway would follow Ab1+ soluble antigen→Ab3'. Following this scheme, MAb-B43.13 (Ab1) would bind the CA125 serum antigen, which would in turn generate an anti-CA125 antibody (Ab3'). Furthermore, the Ab3' antibodies generated under this pathway would bind and be inhibited by B27.1 antibodies, because, as noted above, CA125 is multi-epitopic and B43.13 and B27.1 epitopes are distinct; also, Ab3' will not bind to anti-MAb-B43.13 antibodies.

Thus, if the patients serum contained anti-CA125 antibodies that were inhibitable by MAb-B43.13 only, it was classified as containing Ab3; those inhibitable by MAb-B27.1 were classified as Ab3'.

Results

Fourteen patients developed anti-CA125 antibodies in their sera (Table 1) in response to MAb-B43.13 injection. 10 of these 14 patients had Ab3' while only two patients had Ab3 antibodies in their sera. Two patients also had both the antibodies. The presence of Ab3 in their sera was also confirmed by the ability of these antibodies to bind to the purified rabbit anti-MAb-B43.13 antibody. There were two patients (#2 and #7) who had anti-CA125 antibodies, but were not inhibitable by MAb-B43.13 or MAb B27.1, thereby suggesting that they may have antibodies against CA125, which recognizes epitopes other than B43.13 or B27.1.

These results clearly indicate that when an antibody against a single epitope (B43.13) was injected into a patient an antibody response against the whole antigen is generated which recognizes different epitopes present in the antigen. The presence of Ab3 in some patients could be explained by the likely presence of excess B43.13 epitope in the CA125 due to insufficient binding of the antibody to that epitope or idiotype induction through Pathway I. Nevertheless, the predominant mechanism of the response seems to be through Pathway II. In other words, injecting a monoclonal antibody to a soluble multi-epitopic antigen into a patient having a functioning immune system generates an antibody to the antigen, where the generated antibody is inhibited by antibodies to different epitopes.

TABLE 1

Characterization of Anti-CA125 Antibodies in Patients Injected with MAb-B43.13

| Patient | Inj. # | Days Elapsed After Injection | Anti-CA125 Ab levels | Binding to Anti-MAb-B43.13 (Ab2)† | Inhibition [%]* | | | Classification |
|---|---|---|---|---|---|---|---|---|
| | | | | | CA125 1000 U/mL | B43.13 s. chain** 10 µg/mL | B27.1 F(ab')** 1 µg/mL | |
| 1 | 3 | 0 | 14.8 | + | 62.3 | 42.6 | 5.8 | Ab3 |
| 2 | 1 | 185 | 9.5 | − | 21.6 | −46.9 | −86.9 | Ab3' |
| 3 | 3 | 86 | 25.4 | + | 80.2 | 84.4 | −0.5 | Ab3 |
| | 3 | 207 | 48.7 | + | 91.4 | 94.0 | −9.1 | Ab3 |
| | 4 | 144 | 79.7 | + | 77.1 | 93.0 | 3.5 | Ab3 |
| | 4 | 270 | 30.9 | + | 79.2 | 83.0 | −55.8 | Ab3 |
| | 4 | 309 | 16.7 | + | 77.0 | 83.0 | −55.8 | Ab3 |
| | 5 | 134 | 64.1 | + | 89.1 | 83.3 | −37.3 | Ab3 |
| 4 | 2 | 15 | 23.6 | − | 62.3 | −84.8 | −101.9 | Ab3' |
| | 2 | 41 | 21.6 | − | 56.9 | 20.2 | −7.0 | Ab3' |
| | 2 | 76 | 23.1 | − | 63.6 | 29.4 | 4.5 | Ab3' |
| | 3 | 28 | 11.1 | − | 24.2 | 4.7 | 11.1 | Ab3' |
| 5 | 1 | 16 | 15.5 | + | 74.8 | 78.3 | 39.9 | Ab3'/Ab3 |
| 6 | 3 | 0 | 10.3 | + | 54.0 | 60.2 | 22.7 | Ab3'/Ab3 |
| 7 | | | 14.9 | − | 29.7 | −70.2 | −358.9 | Ab3' |
| 8 | 1 | 7 | 59.1 | − | 77.1 | 87.1 | 34.9 | Ab3' |
| | 1 | 17 | 46.9 | − | 78.4 | 86.5 | 40.7 | Ab3' |
| 9 | 3 | 112 | 9.2 | − | −66.4 | 16.0 | 20.2 | Ab3' |
| | 3 | 166 | 8.5 | − | −18.4 | 42.5 | 56.5 | Ab3' |
| 10 | 3 | 0 | 41.5 | − | 30.8 | 39.2 | 20.0 | Ab3' |
| 11 | 5 | 134 | 8.8 | − | 19.0 | 24.4 | 3.5 | Ab3' |
| | 6 | 134 | 8.7 | − | 18.0 | 39.0 | 46.0 | Ab3' |
| | 9 | 26 | 13.4 | − | 54.5 | 19.3 | 11.1 | Ab3' |
| | 9 | 65 | 13.3 | − | 56.1 | 24.4 | 3.7 | Ab3' |
| | 10 | 40 | 9.4 | − | 61.4 | 37.0 | 33.4 | Ab3' |
| 12 | 2 | 14 | 10.6 | − | 24.5 | −54.4 | 19.9 | Ab3' |
| 13 | 1 | 15 | 11.5 | − | 30.8 | 47.4 | 55.8 | Ab3' |
| 14 | 2 | 17 | 10.1 | − | 30.3 | −51.2 | 1.2 | Ab3' |

*To be considered to be significant, inhibition has to be at least 10%
**Single chain MAb-B43.13 and F(ab') MAb-B27.1 were used in the inhibition studies to avoid non-specific inhibition due to the Fc portion of the antibody and cross-reactivity due to HAMA.
†Anti-MAb-B43.13 (Ab2) was purified from rabbits injected with MabB43.13.

Example 2

In pharmaceutical studies, blood samples were analyzed for CA125 levels before and at selected intervals after MAb-B43.13 injection. In patients with elevated CA125 levels before injection, a significant drop in circulating CA125 levels could be seen immediately after MAb-B43.13 injection (Table 2). This clearly demonstrated that the binding agent upon introduction into the body interacts and removes the circulating CA125.

TABLE 2

CA125 Clearance after MAb-B43.13 Injection

| Time (min) after MAb | Patient # (CA 125 levels are given in U/mL) | | | | | | |
|---|---|---|---|---|---|---|---|
| | 002 | 003 | 004 | 006 | 007 | 008 | 010 |
| 0 | 760 | 68 | 65 | 72 | 90 | 269 | 431 |
| 30 | 210 | 2 | 7 | 21 | 16 | 47 | 141 |
| 60 | 144 | 3 | 0 | 22 | 16 | 60 | 79 |
| 240 | 240 | 0 | 0 | 11 | 15 | 52 | 97 |
| 1440 | 277 | 5 | 3 | 6 | 23 | 59 | 96 |
| 2880 | 404 | — | 5 | 1 | 23 | 67 | 93 |
| 4320 | 429 | — | 7 | — | — | — | — |

Furthermore, antigen complexed with antibody is presented efficiently to the immune system and generates better antigen-specific humoral and cellular response. This demonstrated by the following experiments shown in Examples 3 and 4.

Example 3

Figure 1:
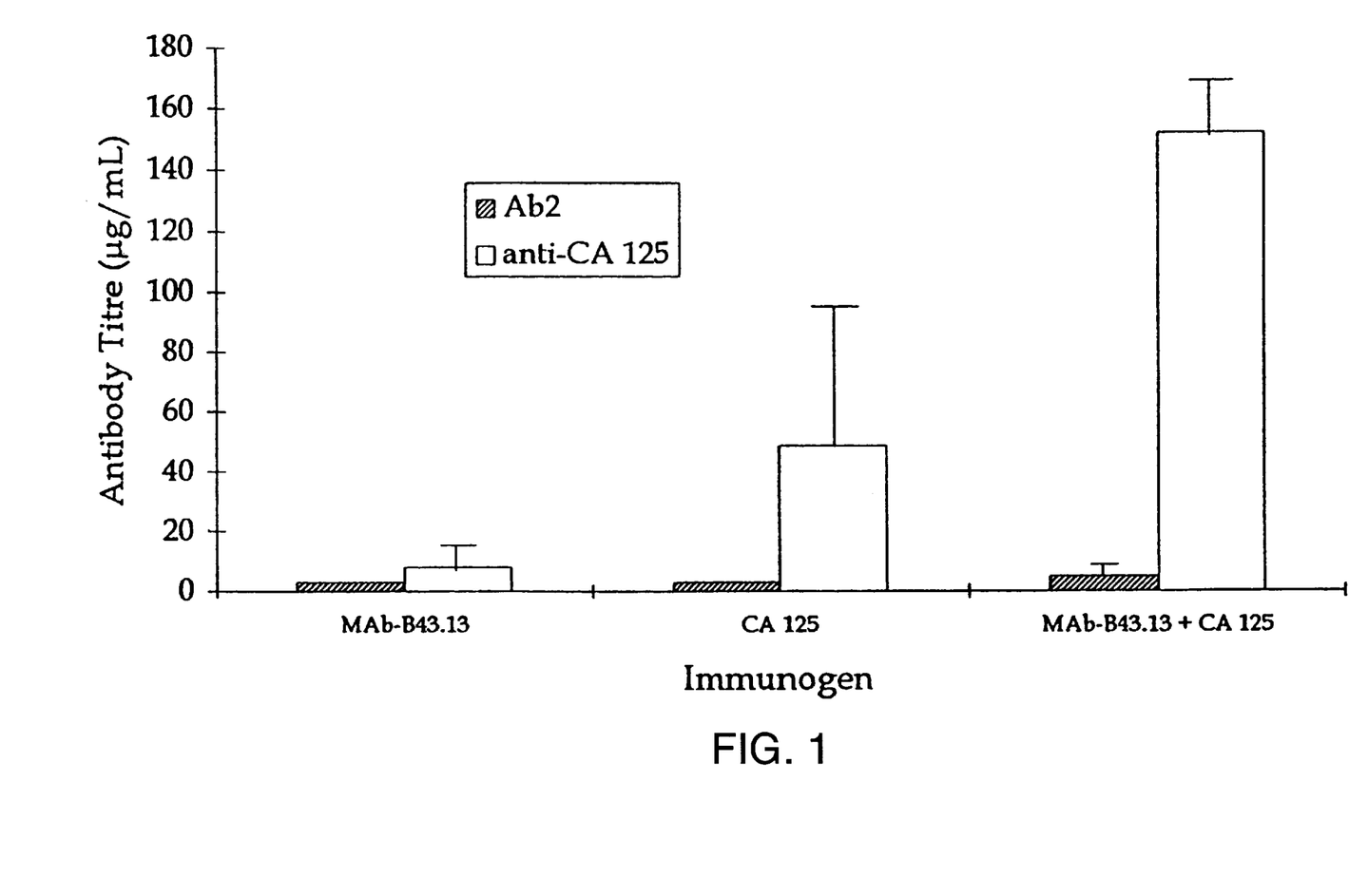
FIG. 1 shows the superior results obtained after immunizing mice with a composition of the present invention, compared to other compositions.

Balb/c mice were immunized either with 10 μg of MAb-B43.13 in PBS, i.v.; 10,00 units of CA125 in PBS, i.v.; or 10 μg of MAb-B43.13 and 10,000 units of CA125 in PBS, i.v., every three weeks for a total of 3 injections. The ratio in the B43.13/CA125 injection was similar to that observed in patients with elevated CA125 levels as determined based on the pharmacokinetics data given in Table 2. When the mice sera were analyzed for anti-CA125 antibody levels, the mice injected with the antigen-antibody complex had the highest titre. Anti-idiotype induction in these balb/c mice are shown graphically in FIG. 1. This supports the observation that binding agent—antigen interaction leads to better antigen specific humoral immune response compared to binding agent or antigen alone.

Example 4

Figure 2:
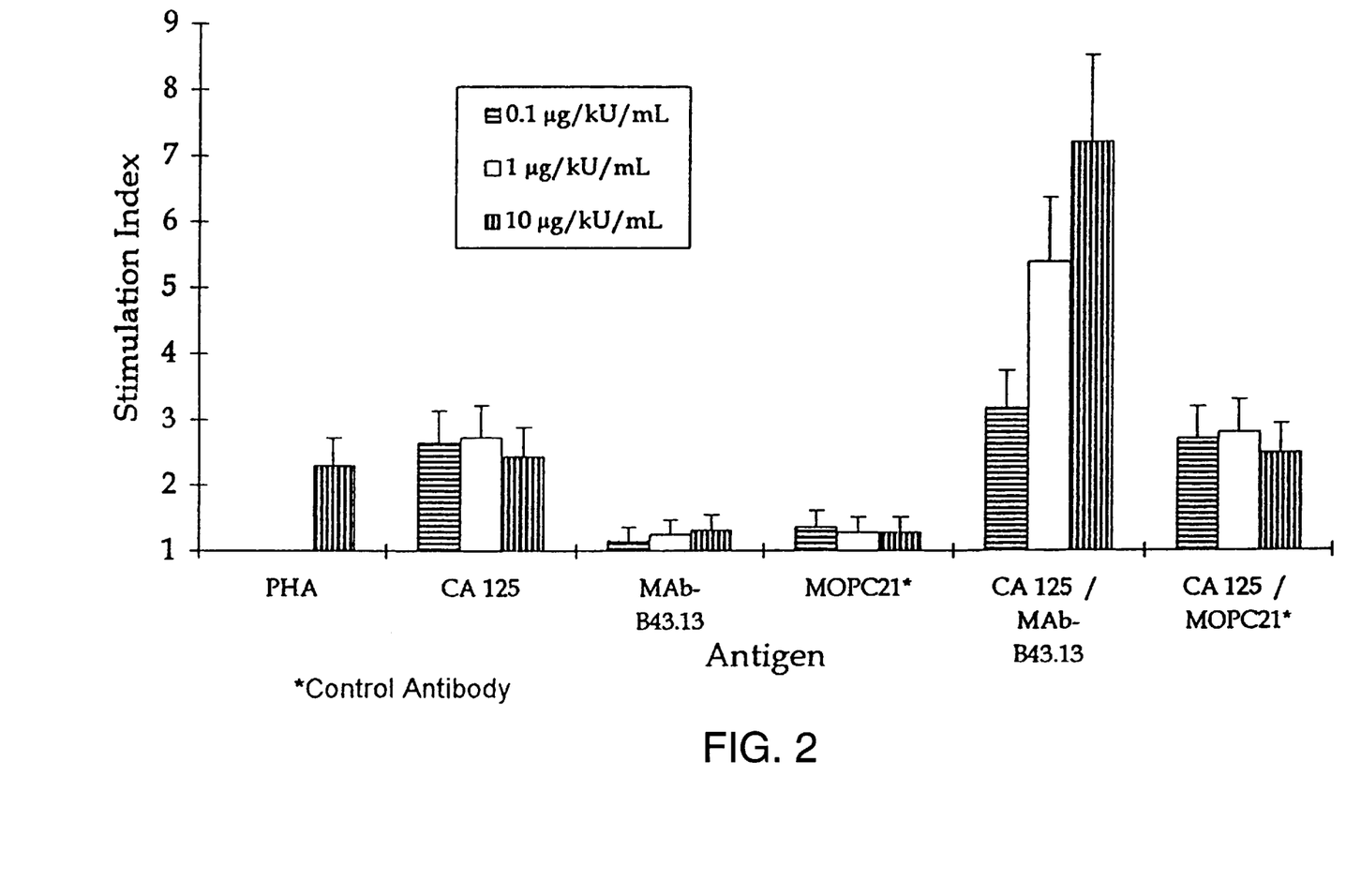
FIG. 2 shows superior macrophage stimulation caused by a composition of the present invention, compared to other compositions.

Similarly, better cellular immune response was observed when the binding agent was presented in association with the antigen to the T-cells. Thus, macrophages isolated from mouse peritoneal cavities were stimulated with MAb-B43.13 alone; CA125 alone, a MAb-B43.13-CA125 complex; or control MAb-CA125 and presented to CA125 specific mouse T-cells (isolated from mice injected with CA125). When the proliferation of T-cells as monitored by [$^3$H]-Thymidine uptake was followed, optimal stimulation index was observed in macrophages stimulated with antibody-antigen complex (FIG. 2).

Example 5

The conclusion in Example 1 was further supported by finding a correlation between serum CA125 levels in patients injected with MAb-B43.13 and human anti-CA125 antibody generation. The findings are shown in Table 3, and support the conclusion that the antigen should be present in the serum for the binding agent to interact; such interaction leads to an antigen-specific humoral response.

TABLE 3

Correlation between Serum CA125 Levels and Antibody Levels in Patients Injected with MAb-B43.13.

| Pre-injection Serum CA125 Level | Anti-CA125 Antibody Titre (No. of Positive/Total Patients) |
|---|---|
| <100 U/mL | 3/29 |
| >100 U/mL | 15/46 |

Example 6

The role of serum antigen in inducing multi-epitopic antibody response as a consequence of an antibody injection was further confirmed in rabbit studies. Rabbits that do not contain any serum CA125, when injected with MAb B43.13, produced anti-CA125 antibodies that were not inhibitable by B27.1. In contrast, ovarian cancer patients with high serum antigen CA125 levels produce anti-CA125 antibodies that are inhibitable by B27.1 in response to MAb-B43.13 injection.

Example 7

Figure 3:
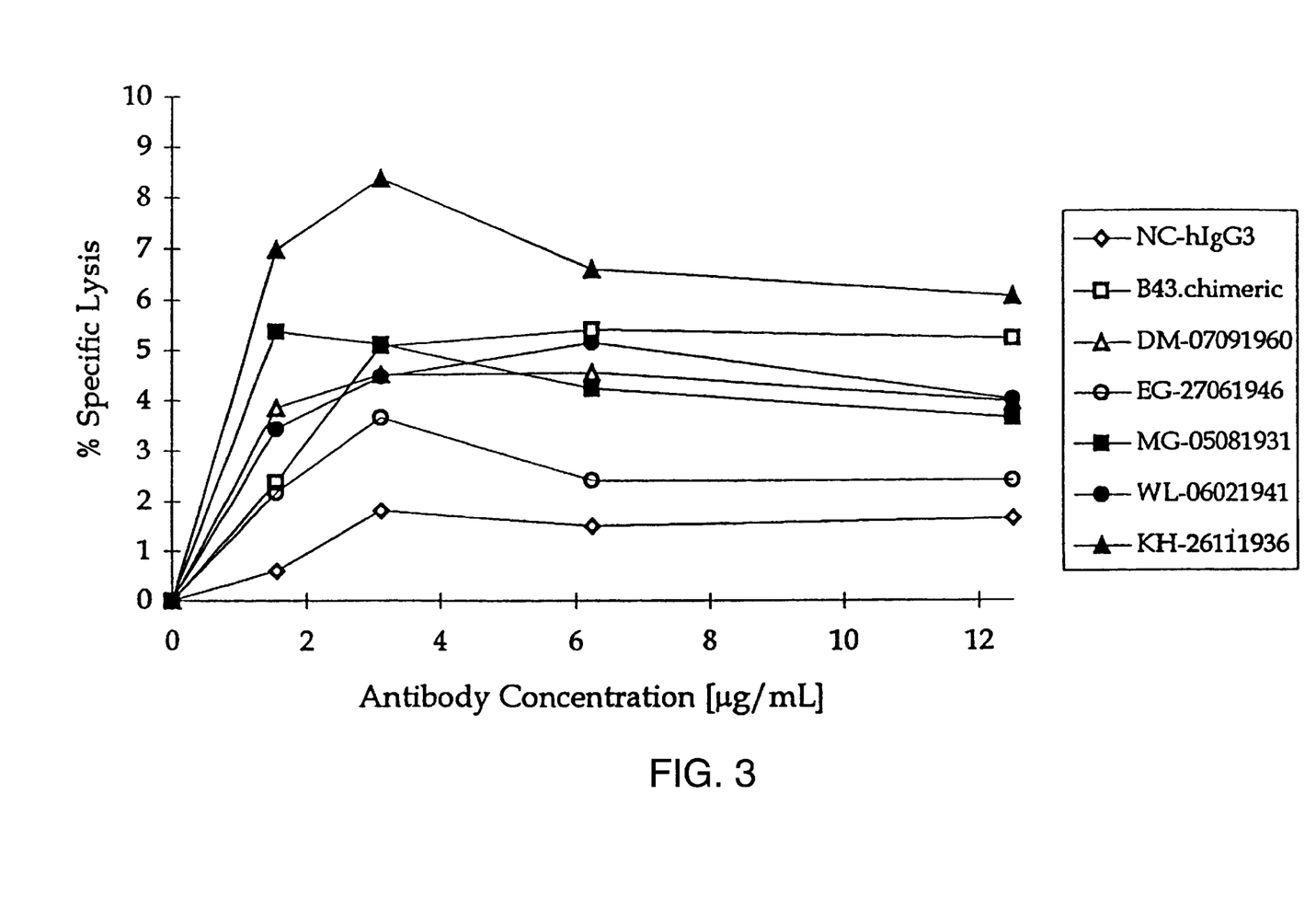
FIG. 3 shows tumor cell lysis caused by administering a composition of the present invention.

Experimental Verification of Induction of Antigen Specific Anti-Tumor Response by Antibody Injection Human anti-CA125 antibody causes tumor cell lysis through antibody dependent cellular cytotoxicity ("ADCC"). Although the injected MAb-B43.13 does not cause by itself an ADCC and/or complement dependent cytolysis ("CDC") mediated lysis of ovarian tumor cells, the generation of anti-CA125 antibodies in patients injected with MAb-B43.13, leads to tumor cell lysis (see FIG. 3). This was studied in a $^5$Chromium release assay by incubating the labeled ovarian tumor cells with effector cells, and sera of six patients injected with MAb-B43.13. This supports the conclusion that the injection of a binding agent leads to its interaction with the antigen, with a specific humoral response resulting in anti-CA125 antibodies that cause tumor cell lysis through ADCC. The results clearly demonstrated the generation of antigen specific anti-tumor response after injection of the antibody.

Example 8

Generation of CA125 Specific Cytotoxic T-lymphocytes in Patients Injected with MAb-B43.13

Similarly injection of the binding agent to the cancer patient containing CA125 lead to antigen specific CTL's. Peripheral Blood Mononuclear Cells (PBMC) from eight patients injected with MAb-B43.13 were tested for cytotoxicity against CA125 positive or CA125 negative ovarian tumor cells in a chromium release assay. The results are shown in Table 4. The specificity of the lysis was confirmed by the ability of MAb-B43.13 to inhibit such lysis, as well as the inability to kill CA125 negative tumor cells. Of the 8 patients who received MAb-B43.13, at least four patients (#5 to #8) were determined to have CA125 specific cytotoxic T lymphocytes (CTL's) in their blood. The generation of CA125 specific CTL's are likely to kill ovarian tumor cells in patients.

TABLE 4

Cytotoxicity In Patients Injected With A Vaccine Containing MAb-B43.13

| PATIENT ID | SAMPLE Injection Number | Days Post Injection | PERCENT LYSIS CAOV-4 | SK-OV-3 | K562 | PERCENT INHIBITION BY MAb-B43.13 (5 µg) | PERCENT DIFFERENCE BETWEEN CA 125 + ve CA 125 − ve CELLS |
|---|---|---|---|---|---|---|---|
| 1 | 2 | 17 | 2.0 | 0.0 | 3.7 | ND* | insignificant |
| 2 | 2 | 0 | 9.8 | 7.5 | 33.5 | ND | 31 |
| 3 | 3 | 0 | 22.8 | 20.4 | 64.3 | ND | 12 |
| 4 | 3 | 0 | 25.8 | 20.2 | 44.5 | 4.7 | 28 |
| 5 | 3 | 0 | 65.1 | 45.4 | 80.7 | ND | 43 |
| 6 | 3 | 0 | 23.1 | 20.0 | 42.0 | 19.2 | 16 |
|   | 3 | 6 | 7.4 | 5.2 | 10.2 | 53.0 | 42 |
| 7 | 4 | 355 | 10.3 | 3.1 | 18.9 | ND | 23 |
| 8 | 10 | 425 | 25.5 | 18.2 | 39.2 | 15.4 | 40 |

*ND = Not Done due to lack of sufficient lymphocytes
Results are the mean of one experiment performed in triplicate Example 9

Tumor killing either through an anti-CA125 antibody-mediated ADCC mechanism or through CA125-specific CLTs, lead to increased survival in patients injected with MAb-B43.13. Although high levels of serum CA125 have been suggested to be a poor prognostic indicator, they seem to have a beneficial effect in combination with the injection of anti-CA125 antibody in such patients. For example, when the CA125 levels were more than 100 units/mL, immune response against CA 125 increased by more than 20% which in turn increased the median survival in those patients from 39.1 months to 54.5 months (Table 5). Thus the injection of a binding agent to a patient containing elevated levels of multiepitopic soluble antigen leads to antigen specific humoral and cellular response which in turn leads to tumor killing followed by improved survival.

TABLE 5

Correlation between Serum CA125 Levels, Human Anti-CA125 (Ab₁') Response and Survival in Patients Injected with MAb-B43.13

| Preinjection Serum CA125 Level | %-age of Patients with Human Anti-CA125 Response | Mean Survival in Month |
|---|---|---|
| <100 U/mL | 10.3% | 39.1 |
| >100 U/mL | 32.6% | 54.5 |

Example 10

One pancreatic cancer patient diagnosed with metastatic disease was repeatedly injected with a composition including an anti-CA 19.9 antibody. The patient received no other treatment, and survived for 22 months after the original diagnosis (19 months after surgery and the injection) This is compared to the current survival period estimate of six months survival after initial diagnosis.

Example 11

Those with skill in the art recognize that the administered dosage can vary widely based on a wide set of different circumstances. The following provides preliminary dosage guidelines.

Retrospective analysis of more than 100 patients who have been injected up to ten times with a 2 mg dose of MAb-B43.13 indicated that some of these patients experienced: a) an unusual course of their disease, characterized by unexpectedly long survival times; and b) no significant adverse reaction or toxicity.

Immunological studies were conducted to understand and evaluate the in vivo mechanism of action of MAb-B43.13. These studies indicated that the extent of anti-idiotypic induction in patients injected with a 2 mg dose of MAb-B43.13 was unrelated to the number of injections or the clinical stage of their disease. However, anti-idiotypic induction is dependent on the levels of the circulating CA 125 present in the patient's sera. Additional experiments demonstrated that the injection of MAb-B43.13 into patients with measurable serum CA 125 led to the formation of antigen-antibody complexes, resulting in antigen epitope presentation and antigen-specific humoral and cellular response to the tumor.

These studies indicate that an effective dose requires only enough antibody to optimally deliver and present all possible circulating CA 125 antigen to the immune system. In vitro studies indicated that 1 ng of MAb-B43.13 can bind 10 units of CA 125. Assuming 40 mL of plasma per kg of body weight, the injection of 2 mg of MAb-B43.13 into a 60 kg patient can bind approximately 8333 U/mL of CA 125 in serum. Since all of the ovarian cancer patients tested to date have had far less than 8333 U/mL of CA 125 in their serum, an injection of 2 mg of MAb-B43.13 is more than sufficient to induce the required immune response. Additionally, in patients that received radiolabeled MAB-B43.13 for immunoscintographic confirmation of the disease, the results of imaging were excellent in spite of high serum CA 125, suggesting that there is excess MAB-B43.13 for specific tumor uptake.

Furthermore, multiple injections at selected intervals appear to provide optimal benefits to patients, since CA 125 is generated throughout the course of the disease.

Finally, the retrospective analysis showed that the 2 mg dose appears to have therapeutic efficacy; none of the patients (>100) have developed any serious side effects or adverse reactions. If the total HAMA response is an indication of anti-idiotypic induction, a 2 mg dose generates significant levels of anti-idiotypic antibodies to product the desired therapeutic benefit. Multiple injections of 2 mg of MAb-B43.13 at selected intervals appears to maintain the anti-idiotypic antibodies at the desired therapeutic level without causing any isotypic HAMA-induced toxicity.

A range of effective doses or a therapeutically acceptable amount of MAb-B43.13 therefore includes, but is not limited to, 2 mg.

Industrial Applicability

The compositions comprising a binding agent according to this invention are particularly useful in compositions containing an immunogenic or therapeutic amount of at least one of the binding agents of the invention. An immunogenic or therapeutic amount is an amount that stimulates an immune response of a humoral, cellular, or combined humoral and cellular nature in the host. The host immune response comprises increased activity against an epitope on a tumor-associated antigen that is different than the epitope to which the binding agent binds. The compositions of the present invention are administered as anti-tumor vaccines to subjects at risk for the development of a malignancy, or to subjects showing a diagnosis of the malignancy. These compositions may be used to prepare a pharmaceutical composition that elicits an immune response.

What is claimed is:

1. A method for inducing the production of antibodies against a multi-epitopic endogenous antigen, wherein said endogenous antigen does not elicit an effective host immune response, the method comprising contacting said multi-epitopic endogenous antigen present in the host with a composition comprising a non-radiolabeled binding agent that specifically binds to a first epitope on said antigen, and allowing the binding agent to form a binding agent/antigen pair, such that a host immune response is elicited against a second epitope on the antigen;

wherein the antigen is CA125 and the binding agent is murine monoclonal antibody B43.13, ATCC. No. PTA-1883.

2. The method of claim 1 wherein the host immune response comprises a cellular and humoral immune response.

3. The method of claim 1 wherein the host immune response comprises a cellular immune response.

4. The method of claim 1 wherein the host immune response comprises a humoral immune response.

5. The method of claim 1 wherein the multi-epitopic antigen is a soluble antigen.

6. The method of claim 5 wherein the soluble antigen is associated with a human disease or condition.

7. The method of claim 6 wherein the human disease or condition is cancer.

8. The method of claim 7 wherein the cancer is ovarian cancer.

9. The method of claim 1 wherein the binding agent is an Ab1 antibody.

10. The method of claim 1 wherein the binding agent/antigen pair is an immunogen.

11. The method of claim 1 wherein the binding agent is a binding moiety that is capable of binding to a single epitope expressed on the antigen.

12. The method of claim 1 wherein the composition comprising a binding agent further comprises one or more adjuvants, one or more carriers, one or more excipients, one or more stabilizers, one or more imaging reagents, one or more pharmaceutically acceptable carriers, and/or physiologically acceptable saline.

13. The method of claim 1 wherein allowing the binding agent to form a binding agent/antigen pair presents epitopes on the antigen, other than the epitope recognized by B43.13, to the host's immune system.

14. The method of claim 13 wherein presenting said epitopes on the antigen to the host's immune system results in generating a humoral and a cell-mediated immune response to said epitopes.

* * * * *

UNITED STATES PATENT AND TRADEMARK OFFICE
CERTIFICATE OF CORRECTION

PATENT NO. : 6,241,985 B1
DATED : June 5, 2001
INVENTOR(S) : Ragupathy Madiyalakan; Antoine A. Noujaim; Richard P. Baum It is certified that error appears in the above-identified patent and that said Letters Patent is hereby corrected as shown below:

<u>Title page,</u>
Delete "Birgit Schultes" name as an inventor.

Include the following three claims:
35. The method of claim 16 wherein contacting administering by an immunologically suitable route.
36. The method of claim 35 wherein adminstering by an immunologically suitable route comprises administering by intravenous, subcutaneous, intraperitoneal, intradermal, intramuscular, or intralymphatic route.
37. The method of claim 35 wherein administering by an immunologically suitable route comprises administering in solution form.

Signed and Sealed this

Twenty-fifth Day of December, 2001

Attest:

*Attesting Officer*

JAMES E. ROGAN
*Director of the United States Patent and Trademark Office*